United States Patent [19]

Pearsall

[11] 4,052,471

[45] Oct. 4, 1977

[54] PROCESS FOR CHLORINATING $C_8$ TO $C_{30}$ LINEAR HYDROCARBONS

[75] Inventor: Mason P. Pearsall, Houston, Tex.

[73] Assignee: Pearsall Chemical Corporation, Houston, Tex.

[21] Appl. No.: 602,244

[22] Filed: Aug. 6, 1975

[51] Int. Cl.² ............... C07C 17/02; C07C 17/08; C07C 17/10
[52] U.S. Cl. ................... 260/660; 260/663; 260/864; 526/72
[58] Field of Search ............ 260/660, 663, 864

[56] References Cited

U.S. PATENT DOCUMENTS

| | | | |
|---|---|---|---|
| 2,022,619 | 11/1935 | Gallsworthy | 260/162 |
| 2,763,699 | 9/1956 | Van Dijk et al. | 260/654 |
| 2,844,599 | 7/1958 | Rendall et al. | 260/389 |
| 3,259,561 | 7/1966 | Sievers | 204/163 |
| 3,454,664 | 7/1969 | Siddiqui et al. | 260/660 |

*Primary Examiner*—Floyd D. Higel
*Attorney, Agent, or Firm*—Kenneth H. Johnson

[57] ABSTRACT

An improved process for chlorinating substantially linear, liquid $C_8$ to $C_{30}$ hydrocarbons by intimately mixing the hydrocarbons and water in a weight ratio of 0.09:1 to 10:1, feeding the mixture of hydrocarbon and water to a reactor, adding 2 to 20 moles of chlorine per mole of hydrocarbon to the mixture in countercurrent flow to the mixture at a rate of 20 to 600 grams per hour per kilogram of hydrocarbon at 50° to 150° C for .5 to 10 hours and recovering chlorinated hydrocarbons.

9 Claims, 1 Drawing Figure

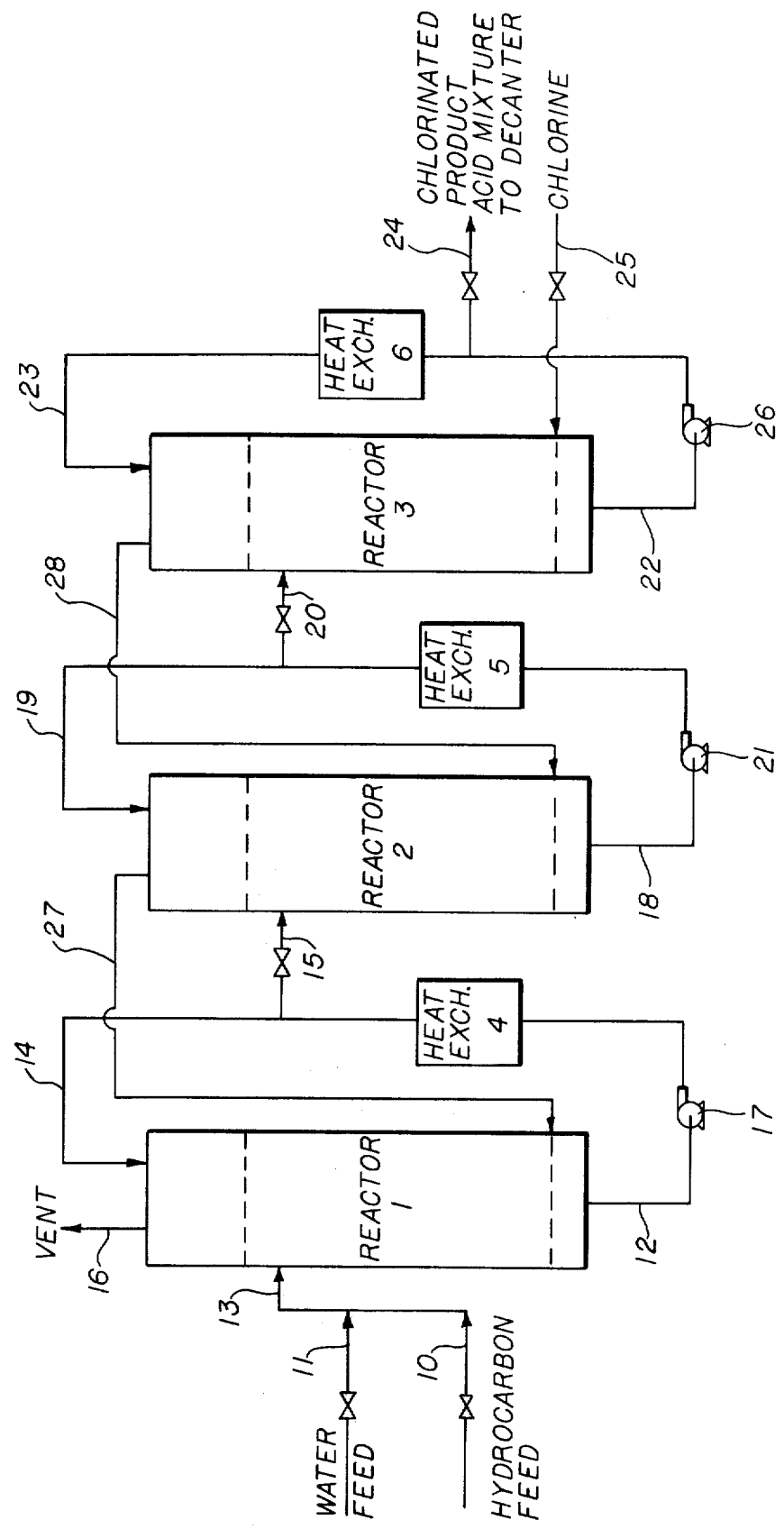

PROCESS FOR CHLORINATING $C_8$ TO $C_{30}$ LINEAR HYDROCARBONS

BACKGROUND OF THE INVENTION

The present invention relates to a process for chlorinating long chain paraffin and olefin hydrocarbons.

In the prior art it has been recognized that contacting a chlorinated product with water is a convenient means of removing by-product HC1. Other processes have combined the chlorination and HC1 removal by chlorinating with an aqueous medium.

For example in U.S. Pat. No. 2,022,619 the patentee prepared a solution of chlorine water by saturating water with chlorine gas in one step and in a separate step agitating the solution with a petroleum oil to form a chlorinated product.

It is an advantage of the present invention that fewer steps are required in the chlorination process. It is a feature of the present invention that it is applicable to long chain paraffins. These and other advantages and features will be apparent from the following description of the invention.

SUMMARY OF THE INVENTION

Briefly stated the present invention is a process for chlorinating long chain paraffins comprising intimately contacting a liquid long chain paraffin with water, contacting said intimate mixture of long chain paraffin and water with gaseous or liquid chlorine, and separating an organic phase and an aqueous phase, said organic phase containing chlorinated paraffins.

DETAILED DESCRIPTION OF THE INVENTION

It can be appreciated that the present process eliminates one step as might be suggested by U.S. Pat. No. 2,022,619, i.e., the separate step of preparing a solution of chlorine which is then employed to chlorinate the petroleum oil. The present process is specific to long chain hydrocarbons, i.e., acyclic hydrocarbons having 8 to 30 carbon atoms, e.g., 8 to 20 carbon atoms. Both olefins and paraffins are suitable for the present process. The chlorination rate may be higher for olefins because of the higher reactivity of the ethylenic unsaturation. The hydrocarbons may contain some branching, however, linear hydrocarbons are preferred and preferably hydrocarbons containing less than 5 weight percent branched hydrocarbons. As a practical matter commercially available hydrocarbons will contain small amounts of branched chains, i.e., as noted above. Similarly the hydrocarbons employed may be a mixture of those in the recited range or substantially pure materials. Commercially available streams will usually contain some degree of mixture. It has been observed that petroleum oils may be suitable for the present process, since the chlorination of petroleum oils according to the present process produced stable emulsions (slack wax is included as an oil).

Suitable long chain hydrocarbons are intimately mixed with water. Generally the weight ratio of hydrocarbon to water is in the range of 0.09:1 to 10:1 and more preferably about 0.2:1 to 5:1. The intimate contacting is obtained by any conventional means, such as turbines, paddles or contact of counter current streams in an appropiately baffled column.

While the hydrocarbon and water are in intimate contact the chlorine is added to the mixture and intimately contacted therein because of the agitation which would normally accompany the intimate contacting of the hydrocarbon and water.

Either gaseous or liquid chlorine may be used in the process. The liquid chlorine may offer an advantage, since the liquid chlorine can provide more chlorine to the mixer-reactor through any given equipment with generally easier handling.

The chlorine is generally added to the hydrocarbon-water mixture at a rate of 20 to 600 grams of chlorine per kilogram of hydrocarbon per hour. The amount of chlorine added may be varied over a wide range, depending on the degree of chlorination desired, but usually a total of about 2 to 20 moles of chlorine per mole of hydrocarbon will be employed, more preferably about 2 to 12 moles of chlorine per mole of hydrocarbon.

Hydrocarbons having over 20 carbon atoms are generally chlorinated up to about 50–55% on a weight basis, since these materials will tend to form solids at over 55% chlorine content. Paraffins of over 20 carbon atoms are frequently referred to as "waxes". Hydrocarbons of 8 to 20 carbon atoms may be chlorinated to 70 weight % or more. In the chlorination one mole of chlorine is required to substitute one atom of chlorine on the carbon chain, and one mole of HCl is formed. The conditions of chlorination, i.e., rates of flow, temperature etc. are adjusted to operate stoichiometrically, or nearly so, such that very little chlorine escapes from the reaction.

The process may be carried out either continously or in batch with the contacting being conducted for from 0.5 to 10 hours or more at temperatures in the range of 50° to 150° C. The upper limit on operating temperature is the boiling point of the materials under the pressure conditions. The process may be operated at sub or super atmospheric pressure, although it is usually operated under substantially atmospheric conditions. Preferably operating temperatures are 70° to 120° C, for example 90° C up to the boiling point of the materials. The adjustment of the various conditions and rates is made within the prescribed ranges to optimize operations and achieve the desired degree of chlorination. The various chlorination catalysts or initiators are not necessary for operation of the present invention, but may be used, e.g., UV light and the like. In a preferred operation carried out continuously, chlorine is introduced in countercurrent flow to the flow of mixed hydrocarbon and water.

One method of carrying out the present process will be described in regard to the FIGURE of the drawing which is a schematic representation.

In the FIGURE the reaction is carried out in three reactors in series. The hydrocarbon feed 10 and the water feed 11 pass into reactor 1 via line 13. The volume ratio of water to hydrocarbon will generally be 1 to 3 volumes of water per volume of hydrocarbon feed. At the other end of the reactor chain, chlorine is fed into reactor 3 via line 25. The amount of chlorine fed is determined by the desired degree of chlorination in the product. The liquid level in each reactor is maintained at any convenient level to provide approximately from 30 minutes to 1 hour holdup time in each reactor and hence, a reasonable contact time between the reactants. In the reactors, the liquid level is designated by the dotted line in the upper portion of the reactor.

The liquid phase which is a mixture of hydrocarbon-water and chlorine and HCl entering reactor 1 via line 27 is recirculated through line 12 by pump 17 through heat exchanger 4 and hence into line 14 into reactor 1. A portion of the stream being recirculated is fed via line 15 into reactor 2. The recirculation through lines 12 and 14 is at a rate of approximately 100 volumes per minute and the feed through line 15 is approximately 3 volumes per minute. In reactor 2, the hydrocarbon-water mixture contacts in countercurrent flow, the stream of HCl and chlorine entering reactor 2 via line 28 from reactor 3. In a similar fashion, the liquid fraction from reactor 2 is pumped via line 18 by pump 21 through heat exchanger 5 and line 19 at about the same recirculation rate as reactor 1, into reactor 2. Similarly about 3 volumes of the liquid material from reactor 2 is passed into reactor 3 via line 20 where the aqueous hydrocarbon mixture is contacted with chlorine, in the liquid form entering through line 25. The recycle of the liquid fraction of reactor 3 through line 22 and pump 26 hence, into line 23 back into the reactor is at about the same rate as reactor 1.

The chlorinated product which is the chlorinated hydrocarbon as well as the HCl aqueous solution is passed via line 24 to a decanter (not shown) for further treatment and purification. For example, the aqueous HCl can be recovered and employed as such in other processes or sold, or subjected to electrolysis to recover chlorine, which can be recycled into the present process. It should be appreciated that although liquid chlorine is the principle feed through line 25 into reactor 3, that gaseous chlorine can also be added thereto and used equally well to achieve the same results. The chlorinated organic phase is easily separated from the aqueous phase in the decanter.

The chlorine feed to the process enters the bottom of reactor 3 at a rate controlled to give the desired chlorine content percentage in the product discharged via line 24. The chlorine partially reacts in reactor 3 and that quantity which is not reacted with the hydrocarbon in reactor 3 goes overhead through line 28 to the bottom of reactor 2. The chlorine fed to the bottom of reactor 2 is partially consumed in the reaction in reactor 2, and that quantity of chlorine which does not react in reactor 2 goes overhead via line 27 to the bottom of reactor 1, where it is reacted with fresh hydrocarbon and water feed. Since most of the chlorine has been reacted with the hydrocarbon in reactors 3 and 2, and since essentially all of the HCl gas resulting from the chlorine reaction has reacted with water in reactors 3 and 2, the remaining chlorine and HCl is readily reacted with water and hydrocarbon feed in reactor 1. The gas vented from the top of reactor 1 via line 16 is practically free of chlorine and HCl. However, in order to preserve the environment, this vent is passed to a caustic scrubber wherein substantially all of the potentially dangerous gases are removed.

The temperature of the reaction in each of the reactors stages can be varied over a wide range, but typically will be between 80° to 110° C. The use of ultraviolet light is recommended in the reactors 2 and 3.

The configuration of the reactors is not critical so long as it allows efficient gas-liquid contacting and some space is provided at the upper end for disengaging the gas from the liquid. Reactor size is not critical however, suitable height diameter ratio for each reactor would be 12 to 1 with approximately ⅜ of the reactor containing the liquid and the upper ⅛ of the reactor being used to disengage the gas from the liquid.

Although the reactor 1 is understood to operate at atmospheric pressure, it is obvious that the pressure in reactor 2 will be equal to the pressure required to introduce the chlorine gas (containing traces of HCl) into the bottom of reactor 1. Similarly the pressure in reactor 3 will be the sum of the pressure developed by the liquid heads in reactors 1 and 2, and the pressure of the chlorine entering the bottom of reactor 3 will be equal to the sum of the liquid heads in reactors 1, 2 and 3.

In the following examples laboratory apparatus operating in substantially the same manner as the apparatus described in the FIGURE was employed. A wide variety conditions and feeds were used to illustrate the operation. In these particular examples gaseous chlorine was employed, however similar runs were carried out using liquid chlorine with substantially the results. The examples are set up in tabular form with all of the conditions and results therein.

In examples 1 and 2, incomplete information is reported, since the product was a stable emulsion in each case. Hence the present process is readily applicable to the $C_8$–$C_{30}$ hydrocarbons it has not been found suitable for those types of materials which would be denoted as "oils", including for example the slack waxes.

The present materials are excellent flame retarding compositions, useful, for example, as an extenders for polymeric materials.

| EXAMPLE | 1 | 2 | 3 | 4 | 5 | 6 | 7 | 8 | 9 | 10 | 11 |
|---|---|---|---|---|---|---|---|---|---|---|---|
| Feed Type | Slack[4] Wax | Slack[5] Wax | Nor[1] Par 12 | Exxon[2] Type E | Exxon Type E | Exxon[3] Type F | Exxon Type F | Exxon Type F | Exxon Type F | Exxon Type E 1075 | Exxon Type F 4000 |
| Grams of Feed | 1992 | 2126 | 1974.3 | 1460 | 1502 | 3000 | 3000 | 3000 | 3000 | 3105 | 776 |
| Grams of $H_2O$ | 4400 | 6000 | 5000 | 6500 | 6500 | 1218 | 1218 | 1100 | 1000 | 1:29 | |
| wt. ration HC/$H_2O$ Chlorine | 1:2.20 | 1:1.28 | 1:2.46 | 1:4.6 | 1:4.3 | 1:0.41 | 1:0.41 | 1:0.37 | 1:0.33 | | |
| Total hours chlorine | | | 10.5 | 8.0 | 8 | 3 | 5.66 | 2.75 | 2.83 | 5.8 | 1.75 |
| Total gms $Cl_2$ | | | 6424 | 4727 | 4500 | 1181 | 1005 | 1065 | 1004 | 3446 | 696 |
| Ave. $Cl_2$ rate gm/hr. | | | 612 | | | 393.7 | 177.2 | 387.2 | 355 | 594 | 397.7 |
| Product ml of Prod. | 3500 | | 3500 | 2000 | 2400 | 4600 | 3730 | 4000 | 3705 | 1594 | 5271 |
| gm of Prod. | | | | 2880 | | 3121 | 3156 | 3380 | 3120 | 2163 | 4301.2 |
| Sp. gr. of Prod. | | | 1.395 at 27° C | 1.440 at 26° C | | 0.872 | 0.846 | 0.852 at 26° C | 0.848 | 1.357 at 28° C | 0.816 at 22° C |
| Gardner color | | | Milky | Milky | | G-1-2 | G-1-2 | 0.9 | 0.9 | Milky | <G2 |
| % $Cl_2$ Analized in Prod. | 42.% | 46.2 | 60.2 | 63.0 | 62.1 | 18.3/19.2 | 15.1 | 16.08 | 15.38 | 58.90 | 8.57 |
| Temp. of | | | | | | | | | | | |

-continued

| EXAMPLE | 1 | 2 | 3 | 4 | 5 | 6 | 7 | 8 | 9 | 10 | 11 |
|---|---|---|---|---|---|---|---|---|---|---|---|
| reaction °C | | | 95° C | 100±4 | | 70 | 70-80 | 75± 5 | 75±5 | 95± 5 | 62-91 |

(1)Exxon Co. U.S.A., Paraffinic solvents, flash point 160° F, Viscosity cs ut 77° F 1.68, at 100° F 1.37.
(2)Exxon Chemical Co. U.S.A., Light paraffins, principally $C_{11}$ & $C_{12}$. Hydrocarbons 97+% linear paraffins.
(3)Exxon Chemical Co. U.S.A., High paraffins, principally $C_{13}$ & $C_{14}$. Hydrocarbons 97+% linear paraffins.
(4)Melting point 120° F; Oil content max. 7.0%; Viscosity SUS 210° F, max. 42, min. 37; Flash pt. min. 375° F.
(5)Melting point 128° F; Oil content max. 2.0%; Viscosity SUS 210° F, max. 41, min. 38; Flash pt. min. 400° F.

The present process provides a means of chlorination, wherein the by-product HCl is substantially completely removed in the countercurrent water flow thereby allowing substantially undiluted chlorine to contact the hydrocarbon feed.

The present process may also be employed to chlorinate polymeric material, such as polyolefins, vinyls, olefin-vinyl copolymers, olefinallyl copolymers, polyamids, acrylics, polystyrene polyesters, naphthalene sulfonic acid-formaldehyde condensation products, coumorenindene, terpenes, phenolics, unsaturated rubbers, such as butyl rubber, ethylene-propylene terpolymer, polychloroprene, styrene-butadiene, polybutadiene and the like.

The lower molecular weight materials, i.e., dimers, trimers, oglimers and similar materials are frequently liquids and may be used as such, however, higher molecular weight solid polymers may be prepared as mixtures of polymer powders and chlorinated as described above. Suitable organic solvents may vary for the different polymers, and suitable solvents for each polymer are readily available from standard chemical and engineering tables, such as Modern Plastics Encyclopedia, yearly editions.

The invention claimed is:

1. A process for chlorinating hydrocarbons comprising:

intimately mixing a substantially linear liquid long chain hydrocarbon having 8 to 30 carbon atoms with water in a weight ratio of 0.09:1 to 10:1, feeding said mixture of hydrocarbon and water to a reactor, adding 2 to 20 moles chlorine per mole of hydrocarbon to said mixture in countercurrent flow to said mixture at a rate of 20 to 600 grams per hour per kilogram of hydrocarbon, contacting said hydrocarbon, water and chlorine for from 0.5 to 10 hours at a temperature in the range of 50° to 150° C and separating an organic phase containing chlorinated hydrocarbons.

2. The process according to claim 1 wherein the chlorine is gaseous.

3. The process according to claim 1 wherein the chlorine is liquid.

4. The process according to claim 1 wherein said hydrocarbon is a paraffin.

5. The process according to claim 1 wherein said hydrocarbon has from 8 to 20 carbon atoms, said chlorining being carried out up to 70 weight %.

6. The process according to claim 1 wherein said hydrocarbon has from 20 to 30 carbon atoms, said chlorining being carried out up to 55 weight %.

7. The process according to claim 1 wherein said hydrocarbons comprise olefins.

8. The process according to claim 1 wherein from about 2 to 20 moles of chlorine per mole of hydrocarbon are employed.

9. The process according to claim 8 wherein from about 2 to 12 moles of chlorine per mole of hydrocarbon are employed.

* * * * *